United States Patent [19]

Weatherholt

[11] Patent Number: 5,509,409
[45] Date of Patent: Apr. 23, 1996

[54] NASAL CANNULA ASSEMBLY

[75] Inventor: Marjorie F. Weatherholt, La Crescenta, Calif.

[73] Assignee: The Living Trust of Marjorie F. Weatherholt, La Crescenta, Calif.

[21] Appl. No.: 304,278

[22] Filed: Sep. 12, 1994

[51] Int. Cl.$^6$ .......................... A61M 16/00; A61M 15/08
[52] U.S. Cl. ................... 128/207.18; 128/200.26; 128/207.17
[58] Field of Search .................... 128/200.26, 207.14, 128/207.17, 207.18, 912, 911, DIG. 26

[56] References Cited

U.S. PATENT DOCUMENTS

| | | | |
|---|---|---|---|
| 2,831,487 | 4/1958 | Tafilaw | 128/350 |
| 3,726,275 | 4/1973 | Jackson et al. | 128/207.18 |
| 3,802,431 | 4/1974 | Farr | 128/207.18 |
| 4,122,857 | 10/1978 | Haerr | 128/DIG. 26 |
| 4,333,468 | 6/1982 | Geist | 128/DIG. 26 |
| 4,336,806 | 6/1982 | Eldridge, Jr. | 128/DIG. 26 |
| 4,457,754 | 7/1984 | Buttaravoli | 128/DIG. 26 |
| 4,583,976 | 4/1986 | Ferguson | 128/DIG. 26 |
| 4,632,670 | 12/1986 | Mueller, Jr. | 128/DIG. 26 |
| 4,660,555 | 4/1987 | Payton | 128/207.18 |
| 4,699,139 | 10/1987 | Marshall et al. | 128/207.18 |
| 4,742,824 | 5/1988 | Payton et al. | 128/207.18 |
| 4,818,320 | 4/1989 | Weichselbaum | 156/227 |
| 4,838,878 | 6/1989 | Kalt et al. | 128/DIG. 26 |
| 4,981,475 | 1/1991 | Haindl | 128/DIG. 26 |
| 5,025,805 | 6/1991 | Nutter | 128/207.18 |
| 5,037,397 | 8/1991 | Kalt et al. | 604/174 |
| 5,117,818 | 6/1992 | Palfy | 128/DIG. 26 |
| 5,147,320 | 9/1992 | Reynolds et al. | 604/174 |
| 5,163,914 | 11/1992 | Abel | 128/DIG. 26 |

Primary Examiner—Edgar S. Burr
Assistant Examiner—V. Srivastava
Attorney, Agent, or Firm—Kelly, Bauersfeld & Lowry

[57] ABSTRACT

An assembly includes a nasal cannula with nostril outlet prongs and a pair of oxygen inlets. A pair of oxygen feed lines are connected at one end to the cannula inlets and at their other ends are adapted for connection to an oxygen tank. Soft, flexible face guards are attached to portions of the cannula running across the face of the patient, and are positioned so as to lie generally adjacent to the cheek of the patient. The face guards, which may be permanently or temporarily attached to the cannula, distributes the force of the cannula against the patient's skin so as to minimize or eliminate skin impressions.

15 Claims, 2 Drawing Sheets

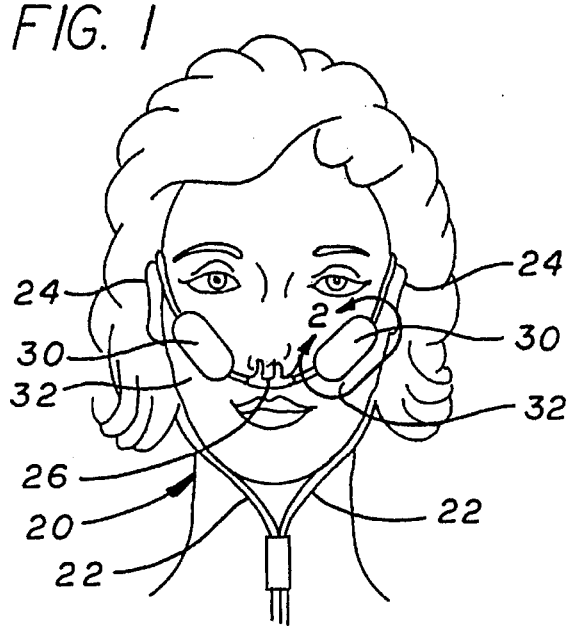
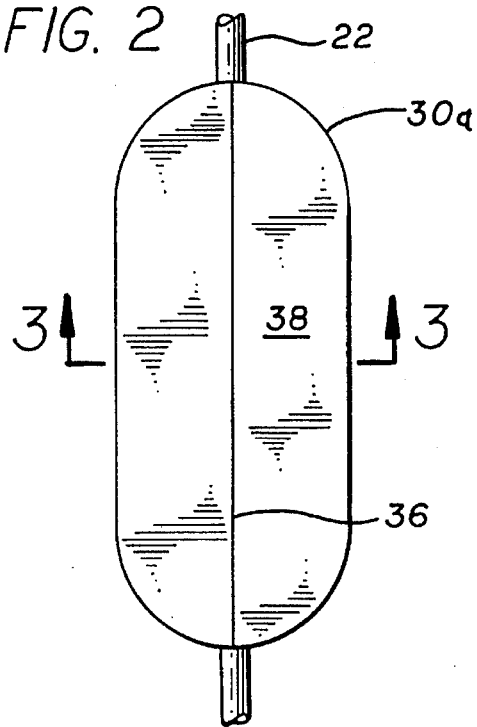
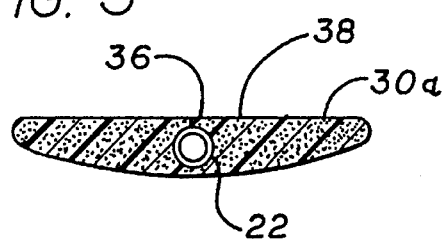
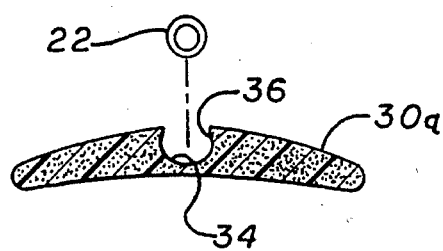
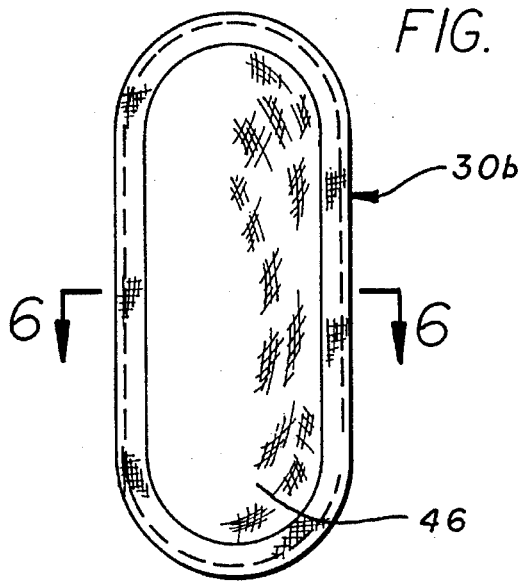
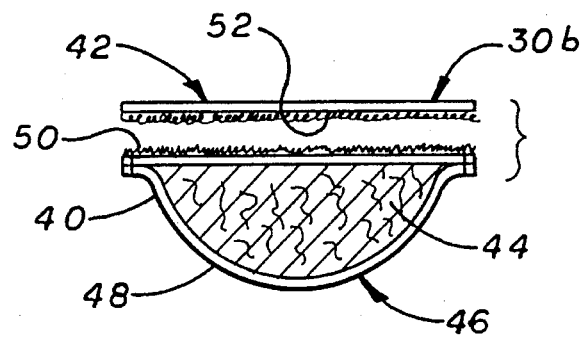

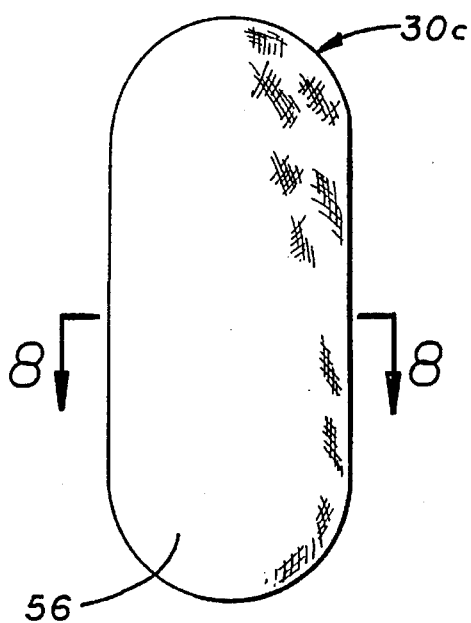
FIG. 7
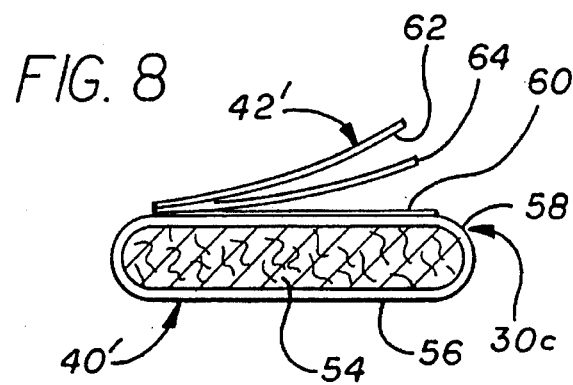
FIG. 8
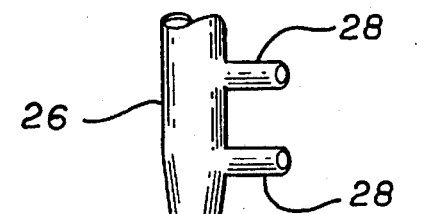
FIG. 9
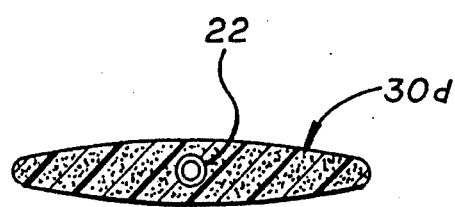
FIG. 10
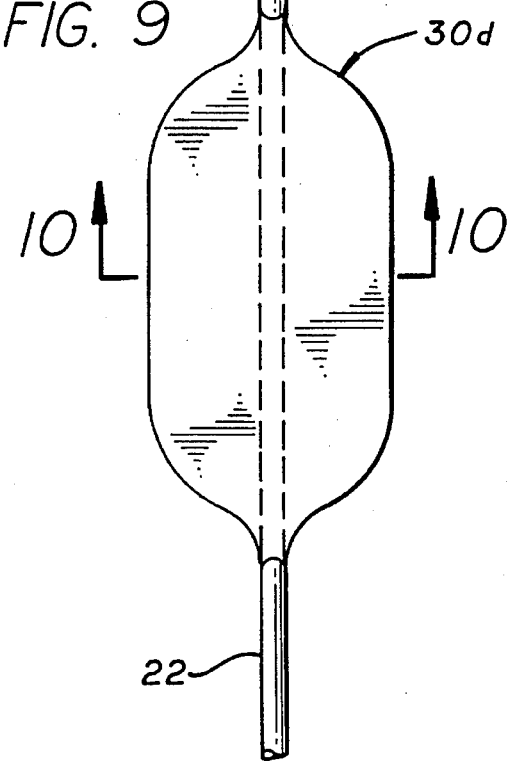

NASAL CANNULA ASSEMBLY

BACKGROUND OF THE INVENTION

This invention relates generally to medical appliances. More specifically, the present invention relates to a nasal cannula assembly.

Nasal cannula assemblies have found widespread use to provide oxygen or other gases to a patient frequently over a relatively long period of time. Such assemblies have largely replaced oxygen masks and provide much greater comfort than nasal catheters. The use of such devices has proved sufficiently beneficial so that they are widely used not only by respiratory patients, but also for a wide variety of patients who require less energy to breathe with the added oxygen supplied by such assemblies.

The most commonly used arrangement includes a dual prong nose piece which is centered in a loop of vinyl tubing. The nose piece openings are inserted in the nose with the tubing tucked behind the ears. A slide adjustment may be used to draw it tight beneath the chin.

Because of the resulting patient benefit, such assemblies are often used over a relatively long period of time. Such use can cause irritation and discomfort. The discomfort arises from the cannula's placement against the face of the patient, which constantly bears against the patient's skin. In some cases the discomfort can reach severe proportions and result in sores similar to bed sores which make it very difficult to continue using the assembly. The result is that patients often remove the cannula assembly entirely due to discomfort at periods of time when the continued use of oxygen is believed medically necessary.

Nasal cannula assemblies are often used with ambulatory patients who are prescribed oxygen therapy by their physicians. Such patients usually transport oxygen with them as they more or less carry-on normal daily activities, and wear the nasal cannula assembly as described above as often as possible. Such people will typically sleep with the cannula in place at night. The tubing across the face leaves an unsightly, deep and irritating impression that becomes semi-permanent so long as the oxygen therapy continues. These impressions in the face of the patient are cosmetically undesirable and, in some cases, provide a disincentive to the use of a nasal cannula assembly by one who would be benefited therefrom.

Accordingly, there has been a need for an improved nasal cannula assembly capable of eliminating the formation of skin impressions. Such an improved nasal cannula assembly should represent a modification of existing assemblies without interfering or altering their present medically beneficial purposes. The present invention fulfills these needs and provides other related advantages.

SUMMARY OF THE INVENTION

The present invention resides in an improved nasal cannula assembly capable of eliminating the face impressions typically left by oxygen feed tubes stretched across a user's face. The assembly comprises a nasal cannula having a pair of apertured nostril outlet prongs and a pair of oxygen inlets. A pair of oxygen feed tubes, each having an inlet and an outlet, are connected to the cannula inlets at one end and to a source of pressurized oxygen at another end. A plate-like face guard of a soft resilient material is mounted over and around each of the feed tubes for purposes of lifting an adjacent portion of the feed tubes away from the user's face. Typically, the face guards are positioned over the user's cheeks.

In one preferred form of the invention, each face guard comprises a single molded component of an elastomeric material which is removably positionable on the respective feed tube. Each face guard includes a cutaway portion intermediate its ends for receiving and supporting the respective feed tube therein. A continuous slit adapted to be flexed open provides access to the cutaway portion. Thus, flexion of the face guard opens the slit and permits the feed tube to be placed within the cutaway portion at the desired location along the length of the feed tube.

In another preferred form, each face guard includes a first portion which underlies the respective feed tube to provide an enlarged, face-engaging cushioned pad, and a second portion which overlies the respective feed tube. The first portion and the second portion cooperatively secure the feed tube therebetween. The first portion comprises a soft batting material within a flexible enclosure. Hook and loop fasteners provide means for fastening the first portion to the second portion.

A third preferred form of the invention is similar to the second embodiment, except that the second portion comprises an adhesive-coated tape. More particularly, the first portion underlies a respective feed tube to provide a generally rectangular face-engaging pillow-like cushioned pad comprising a batting material within a flexible enclosure, wherein the width of the cushioned pad is substantially greater than the diameter of the respective feed tube. The first portion includes an upper surface to which the adhesive-coated tape is adhered, and a non-stick release paper is provided between the first and second portions. The release paper is removable prior to placement of the face guard over and around the respective feed tube. This particular embodiment is most desirable in applications where a disposable face guard is desirable, and in such a case the batting material of the first portion is preferably a paper pulp batting.

A fourth preferred form of the invention is similar to the first embodiment described above except that the face guard is molded directly onto a desired portion of the respective feed tube.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an environmental view illustrating the positioning of a nasal cannula assembly embodying the present invention on the face of a patient;

FIG. 2 is an enlarged partially fragmented view of the area indicated by the number 2 in FIG. 1, showing one embodiment of a face guard secured to a portion of a cannula to provide a cushion between the cannula and the face of the patient;

FIG. 3 is an enlarged sectional view taken generally along the line 3—3 of FIG. 2;

FIG. 4 is a sectional view similar to that shown in FIG. 3, illustrating flexion of the face guard in order to open a slit through one side thereof and place the cannula within the face guard;

FIG. 5 is an enlarged front elevational view of a second embodiment of a face guard of the assembly of the present invention;

FIG. 6 is an enlarged exploded sectional view taken along the line 6—6 of FIG. 5, illustrating the specific construction of a washable face guard;

FIG. 7 is an enlarged front elevational view of a third embodiment of a face guard of the assembly of the present invention;

FIG. 8 is an enlarged sectional view taken generally along the line 8—8 of FIG. 7, illustrating the construction of a disposable version of the face guard;

FIG. 9 is an enlarged front elevational view of a fourth embodiment of a face guard of the assembly of the present invention, wherein the face guard is permanently attached to a portion of the cannula; and FIG. 10 is an enlarged sectional view taken generally along the line 10—10 of FIG. 9.

DETAILED DESCRIPTION OF THE PREFERRED EMBODIMENTS

As shown in the drawings for purposes of illustration, the present invention is concerned with an improved nasal cannula assembly, generally designated in FIG. 1 by the reference number 20. The nasal cannula assembly 20 comprises a pair of oxygen feed tubes 22 whose inlets are connected to a source of pressurized oxygen (not shown). The two oxygen feed tubes 22 are looped over the patient's ears 24 and extend to inlet openings on opposite sides of a conventional nasal cannula 26 which has a pair of nostril outlet prongs 28.

In accordance with the present invention, a pair of plate-like face guards 30 of a soft resilient material are mounted over and around the feed tubes 22. The face guards 30 are preferably positioned over the user's cheeks 32 to lift an adjacent portion of the feed tubes 22 away from the user's face and prevent the formation of skin impressions which may form if the feed tubes 22 are permitted to lie adjacent to the face.

In a first embodiment of the invention shown in FIGS. 2–4, the face guards 30a each comprise a single molded component of an elastomeric material which is removably positionable upon a selected portion of the respective feed tube 22 intermediate the nasal cannula 26 and the ears 24 of the patient. The face guard 30a includes a cutaway portion 34 intermediate its ends for receiving and supporting a respective one of the feed tubes 22 therein. To accomplish this, a continuous slit 36 is provided over the cutaway portion 34 and in alignment therewith through a top surface 38 of the face guard 30a. As the face guard 30a is flexed from a "normal" configuration (shown in FIG. 3) to the configuration shown in FIG. 4, the slit 36 is opened to provide access to the cutaway portion 34, which permits placement of a respective one of the feed tubes 22 therein. The face guard 30a is resiliently biased so that as the flex forces are removed from the face guard, it will return to its "normal" configuration as shown in FIG. 3 to securely retain the feed tube 22 therein.

With reference to FIGS. 5 and 6, a second type of face guard 30b is illustrated. The face guard 30b includes a first portion 40 which underlies the feed tube 22 to provide an enlarged, face-engaging cushioned pad, and a second portion 42 which overlies the respective feed tube. The first portion 40 and the second portion 42 cooperatively secure the feed tube 22 therebetween.

More specifically, the first portion 40 of the face guard 30b comprises a synthetic batting material 44 within a flexible enclosure 46. The flexible enclosure 46 comprises an underlying cloth lining 48 which is sewn to an overlying strip of Velcro hook tape 50. The second portion 42 of the face guard 30b is simply a strip of Velcro loop tape 52 whose dimensions match the Velcro hook tape 50 of the first portion 40.

The particular construction of the face guard 30b provides a washable face guard ideal for home use. The user simply places the portion of the respective feed tube 22 between the segments of hook and loop tape 50 and 52, and presses the second portion 42 against the first portion 40 so as to secure the feed tube 22 therebetween. The face guard 30b may be slid along the length of the feed tube 22 between the nasal cannula 26 and the ear 24 to position the face guard 30b in the position where it most widely and comfortably distributes the pressure of the feed tube 22 on the face of the user.

With respect to a third embodiment of the face guard 30c as shown in FIGS. 7 and 8, the face guard is attached to a small segment of a respective feed tube between the nasal cannula and a portion of the feed tube adapted to be looped over the user's ear to lift an adjacent portion of the feed tube away from the user's face and prevent irritation thereof. The face guard is again provided with a first portion 40' which underlies the respective feed tube 22 to provide an enlarged face engaging pillow-like, rectangular cushioned pad having rounded edges, and a second portion 42' which overlies the respective feed tube. More specifically, the first portion 40' comprises a paper pulp batting or the like 54 within a paper or plastic enclosure 56. The width of the face guard taken perpendicular to a longitudinal axis of the small segment of the respective feed tube to which the face guard is attached, is substantially greater than the diameter of the feed tube. As shown in the drawings, the length to width ratio of the face guard is approximately 3:1, with the width typically in the range of 1 inch to 1.5 inch. The top surface 58 of the first portion 40' is provided an adhesive coating 60.

The second portion 42' comprises an adhesive-coated tape 62. The feed tube 22 is secured to the face guard 30c by simply placing the feed tube over the adhesive coating 60 of the first portion 40', and then pressing the adhesive coated tape 62 over the feed tube 22 and onto the adhesive coating 60. Thus, the embodiment shown in FIGS. 7 and 8 provides a disposable form of face guard 30c which is ideal for use in hospitals and nursing homes.

To prevent the adhesive coated tape 62 from prematurely adhering to the adhesive coating 60, a non-stick release paper 64 is interposed therebetween during the manufacturing process. The release paper 64 is removed from the between the adhesive coated tape 62 and the adhesive coating 60 at the time the feed tube 22 is placed therebetween.

A fourth embodiment of the face guard 30d is illustrated in FIGS. 9 and 10. Here, the face guard 30d is molded over a respective one of the feed tubes 22 to form an integral unit therewith. The first and fourth embodiments 30a and 30d are preferably manufactured of a clear elastomeric material to make the face guards less noticeable when worn in public.

From the foregoing it is to be appreciated that the face guard s 30a–30d all serve to lift an adjacent portion of the feed tube away from the user's face and prevent irritation thereof. The face guards 30a–30d each have sufficient width to evenly spread the force or pressure of the feed tube 22 against the face and to prevent the formation of impressions in the user's skin. The face guards 30 may be manufactured in a variety of different configurations to accommodate particular circumstances and needs, as shown, all in a simplified fashion to provide an economical improvement to standard nasal cannula assemblies.

Although several embodiments of the invention have been described in detail for purposes of illustration, various modifications of each may be made without departing from the spirit and scope of the invention. Accordingly, the invention is not to be limited, except as by the appended claims.

I claim:

1. A nasal cannula assembly, comprising:

a nasal cannula having a pair of apertured nostril outlet prongs and a pair of oxygen inlets;

a pair of oxygen feed tubes, each tube having an inlet and an outlet, the tubes' outlets being connected to the cannula inlets respectively, and the feed tube inlets being adapted for connection to a source of pressurized oxygen, each of the feed tubes intermediate their ends adapted to be looped over a user's ears, respectively; and a pair of face guards attached to respective small segments of the feed tubes between the nasal cannula and portions of the feed tubes adapted to be looped over the user's ear to lift an adjacent portion of the feed tubes away from a user's face and prevent irritation thereof, each face guard having a surface adapted to rest against a user's face and including a pillow-like, rectangular cushioned pad of soft batting material within a flexible enclosure having rounded edges, disposed between the feed tube and the user's cheek, wherein the width of each face guard taken perpendicular to a longitudinal axis of the small segment of the respective feed tube to which the face guard is attached, is substantially greater than the diameter of the feed tube, said surface adapted to rest against a user's face being totally free of adhesive.

2. The nasal cannula assembly of claim 1, wherein each face guard includes a first portion comprising the pillow-like cushioned pad, and a comparatively thin second portion which overlies the respective feed tube and, with the first portion, cooperatively secures the feed tube therebetween.

3. The nasal cannula assembly of claim 2, including means for fastening the first portion to the second portion.

4. The nasal cannula assembly of claim 3, wherein the fastening means comprises hook and loop fasteners.

5. The nasal cannula assembly of claim 3, wherein the fastening means comprises an adhesive.

6. The nasal cannula assembly of claim 5, wherein the second portion comprises an adhesive-coated tape, and wherein the first portion includes an upper surface to which the adhesive-coated tape is adhered.

7. The nasal cannula assembly of claim 6, including non-stick release paper between the first and second portions of the face guard, which release paper is removable prior to attaching the face guard to the respective feed tube.

8. A nasal cannula assembly, comprising:

a nasal cannula having a pair of inlets;

a pair of feed tubes, each tube having an inlet and an outlet, the tube outlets being connected to the cannula inlets respectively; and face guard means attached to small segments of the feed tubes, for lifting an adjacent portion of the feed tubes away from a user's face to prevent irritation thereof, the face guard means having a surface adapted to rest against a user's face and including a generally rectangular pillow-like cushioned pad of soft batting material within a flexible enclosure having rounded edges and disposed between a respective feed tube and a user's cheek, said surface adapted to rest against a user's face being totally free of adhesive, and means for fastening the cushioned pad to the respective feed tube in a manner which will minimize localized pressure to a user's cheek adjacent the face guard means when a force is applied to the face guard means opposite a user's cheek.

9. The nasal cannula assembly of claim 8, wherein the fastening means comprises an adhesive-coated tape.

10. The nasal cannula assembly of claim 9, wherein the cushioned pad includes an upper surface to which the adhesive-coated tape is adhered.

11. The nasal cannula assembly of claim 10, including non-stick release paper between the adhesive-coated tape and the upper surface of the cushioned pad, which release paper is removable prior to mounting the face guard means to the respective feed tube.

12. A nasal cannula assembly, comprising:

a nasal cannula having a pair of inlets;

a pair of feed tubes each having an inlet and an outlet, the tube outlets being connected to the cannula inlets respectively; and face guard means attached to the feed tubes, for lifting an adjacent portion of the feed tubes away from a user's face to prevent irritation thereof, the face guard means having a surface adapted to rest against a user's face and including a first portion which underlies a respective feed tube to provide a generally rectangular face-engaging cushioned pad comprising a batting material within a flexible enclosure, wherein the width of the cushioned pad is substantially greater than the diameter of the respective feed tube, and a comparatively thin second portion which overlies the respective feed tube and, with the first portion, cooperatively secures the feed tube therebetween, said surface adapted to rest against a user's face being totally free of adhesive.

13. The nasal cannula assembly of claim 12, including hook and loop fasteners for fastening the first portion to the second portion.

14. The nasal cannula assembly of claim 12, wherein the second portion comprises an adhesive-coated tape, and wherein the first portion includes an upper surface to which the adhesive-coated tape is adhered, to provide means for fastening the first portion to the second portion.

15. The nasal cannula assembly of claim 14, including non-stick release paper between the first and second portions of the face guard, which release paper is removable prior to placement of the face guard means over and around the respective feed tube.

* * * * *